(12) United States Patent
Entenman et al.

(10) Patent No.: US 8,620,149 B2
(45) Date of Patent: *Dec. 31, 2013

(54) FLUID WARMING CASSETTE AND SYSTEM CAPABLE OF OPERATION UNDER NEGATIVE PRESSURE

(75) Inventors: Scott Allen Entenman, St. Paul, MN (US); Keith J. Leland, Plymouth, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 1364 days.

This patent is subject to a terminal disclaimer.

(21) Appl. No.: 11/818,880

(22) Filed: Jun. 15, 2007

(65) Prior Publication Data
US 2007/0242934 A1 Oct. 18, 2007
US 2009/0148143 A9 Jun. 11, 2009

Related U.S. Application Data

(63) Continuation of application No. 10/397,942, filed on Mar. 25, 2003, now Pat. No. 7,394,976.

(51) Int. Cl.
*A61F 7/00* (2006.01)

(52) U.S. Cl.
USPC ............ 392/470; 604/107; 604/113; 165/167

(58) Field of Classification Search
None
See application file for complete search history.

(56) References Cited

U.S. PATENT DOCUMENTS

| 2,979,310 | A | 4/1961 | Nicholson | 257/247 |
| 2,992,545 | A | 7/1961 | Walker | 62/515 |
| 3,140,716 | A | 7/1964 | Harrison et al. | 128/399 |
| 3,424,238 | A | 1/1969 | Leeds et al. | 165/133 |
| 3,485,245 | A | 12/1969 | Lahr et al. | 128/272 |
| 3,640,283 | A | 2/1972 | Bhatia | 128/399 |
| 4,131,200 | A | 12/1978 | Rinfret | 206/484 |
| 4,227,525 | A | 10/1980 | Lundquist | 128/214 |
| 4,476,685 | A | 10/1984 | Aid | 62/3 |
| 4,568,330 | A | 2/1986 | Kujawski et al. | 604/53 |
| 4,574,876 | A | 3/1986 | Aid | 165/46 |

(Continued)

FOREIGN PATENT DOCUMENTS

| DE | 0 096 191 | 4/1983 | ............. A61M 5/00 |
| DE | 0 119 469 | 9/1984 | ............... A61J 1/00 |

(Continued)

OTHER PUBLICATIONS

Whittington's Dictionary of Plastics, Third Edition, pp. 434-435.

(Continued)

*Primary Examiner* — Thor Campbell
(74) *Attorney, Agent, or Firm* — X. Christina Huang; Adam M. Bramwell; Terrance A. Meador

(57) ABSTRACT

A fluid warming cassette for use in a fluid warming system includes a first sheet, a second sheet and a flexible spacer having a serpentine opening. At least one of the first and second sheets is a flexible plastic sheet. The spacer is positioned between the first and second sheets and the first and second sheets are joined together over the spacer to form a fluid container having a fluid channel. The fluid container includes a fluid channel with inlet and outlet ports in fluid communication with the fluid channel. The fluid warming cassette is capable of operating under negative pressure without collapse of the fluid channel in the cassette.

14 Claims, 4 Drawing Sheets

(56) References Cited

U.S. PATENT DOCUMENTS

| | | | |
|---|---|---|---|
| 4,602,910 A | 7/1986 | Larkin | 604/87 |
| 4,707,587 A | 11/1987 | Greenblatt | 219/299 |
| 4,709,534 A | 12/1987 | Sengewald | 53/452 |
| 4,731,072 A | 3/1988 | Aid | 604/408 |
| 4,734,269 A | 3/1988 | Clarke et al. | 422/310 |
| 4,744,414 A | 5/1988 | Schon | 165/167 |
| 4,847,470 A | 7/1989 | Bakke | 219/299 |
| 4,887,913 A | 12/1989 | Sengewald | 383/96 |
| 4,919,134 A | 4/1990 | Streeter | 128/400 |
| 4,919,326 A | 4/1990 | Deiger | 229/109 |
| 5,098,202 A | 3/1992 | Rosenbaum | 383/67 |
| 5,102,234 A | 4/1992 | Levy | 383/38 |
| 5,106,373 A | 4/1992 | Augustine et al. | 604/113 |
| 5,125,069 A | 6/1992 | O'Boyle | 392/465 |
| 5,205,348 A | 4/1993 | Tousignant et al. | 165/46 |
| 5,245,693 A | 9/1993 | Ford et al. | 392/470 |
| 5,254,094 A | 10/1993 | Starkey et al. | 604/113 |
| 5,381,510 A | 1/1995 | Ford et al. | 392/470 |
| 5,423,421 A | 6/1995 | Inoue et al. | 206/219 |
| 5,520,975 A | 5/1996 | Inoue et al. | 428/35.9 |
| 5,733,619 A | 3/1998 | Patel et al. | 428/36.91 |
| 5,792,526 A | 8/1998 | Watanabe et al. | 428/35.7 |
| 5,865,309 A | 2/1999 | Futagawa et al. | 206/219 |
| 5,875,282 A | 2/1999 | Jordan et al. | 392/470 |
| 6,175,688 B1 | 1/2001 | Cassidy et al. | 392/470 |
| 6,464,666 B1 | 10/2002 | Augustine et al. | 604/113 |
| 6,535,689 B2 | 3/2003 | Augustine et al. | 392/470 |
| 6,539,172 B2 | 3/2003 | Akahane | 392/470 |
| 6,608,968 B2 | 8/2003 | Bakke | 392/470 |
| 6,673,098 B1 | 1/2004 | Machold et al. | 607/96 |
| 6,775,473 B2 | 8/2004 | Augustine et al. | 392/470 |
| 6,901,216 B2 | 5/2005 | Jusiak et al. | 392/470 |
| 7,010,221 B2 | 3/2006 | Augustine et al. | 392/470 |
| 2002/0081109 A1 | 6/2002 | Mitsunaga et al. | 392/470 |
| 2002/0193739 A1 | 12/2002 | Augustine et al. | 604/113 |
| 2004/0026068 A1 | 2/2004 | Schmidt et al. | 165/46 |
| 2004/0190885 A1 | 9/2004 | Entenman et al. | 392/470 |
| 2007/0173759 A1 | 7/2007 | Augustine et al. | 604/113 |

FOREIGN PATENT DOCUMENTS

| | | | |
|---|---|---|---|
| EP | 0 095 526 | 4/1983 | B32B 27/30 |
| EP | 0 206 419 | 6/1986 | F28F 3/14 |
| WO | WO 93/10416 | 5/1998 | F28F 21/00 |
| WO | WO 00/53246 | 9/2000 | A61M 5/44 |
| WO | WO 01/26719 | 4/2001 | A61M 5/44 |

OTHER PUBLICATIONS

Medi-Temp II Blood/Fluid Warmer, 1 pg, double sided.
Written Opinion mailed Jul. 27, 2001 for PCT Application PCT/US00/02630, published as WO 01/26719.
IPER mailed Jan. 11, 2002 for PCT Application PCT/US00/02630, published as WO 01/26719.

FLUID WARMING CASSETTE AND SYSTEM CAPABLE OF OPERATION UNDER NEGATIVE PRESSURE

PRIORITY

This is a continuation of U.S. patent application Ser. No. 10/397,942, filed Mar. 25, 2003.

RELATED APPLICATIONS

The following co-pending, commonly-assigned patent applications contain subject matter directed to fluid warming and to construction of fluid warming devices:

U.S. patent application Ser. No. 10/822,580, filed Apr. 12, 2004 for "Warming Cassette with Rails and a Stiffening Member";

U.S. patent application Ser. No. 11/257,831, filed Oct. 25, 2005 for "Intravenous Fluid Warming Cassette";

U.S. patent application Ser. No. 11/789,515, filed Apr. 24, 2007 for "Heat Exchanger for High Flow Rate Infusion";

U.S. patent application Ser. No. 11/789,523, filed Apr. 24, 2007 for "High Flow Rate Infusion Unit and Heat Exchanger"; and, U.S. patent application Ser. No. 11/789,752, filed Apr. 24, 2007 for "Bubble Trap for High Flow Rate Infusion".

FIELD OF THE INVENTION

This invention is generally related to parenteral fluid warming systems and devices. More particularly, the invention relates to the structure of a fluid warming cassette used with a warming apparatus to heat parenteral fluid for administration to patients, in which the fluid warming cassette is capable of functioning under negative fluid pressure.

BACKGROUND OF THE INVENTION

Fluid warming systems designed to warm parenteral fluids and blood products (hereinafter "fluids") for infusion into a patient are in common use. Generally, such systems include a warming unit and a flow path device constructed to operate cooperatively with the warming unit by conducting fluid through a flow path in a heating region of the warming unit where the heat is transferred to the fluid as it flows. For example, parenteral fluid warming equipment may include a conductive warming unit and a fluid warming cassette that may be removably received in the warming unit. The fluid warming cassette typically includes a fluid container with a structure designed for being received and supported in the warming unit. Such a fluid container consists of sheets of plastic film material and/or thin metal foil joined, usually by heat or adhesives, to define a fluid channel. Inlet and outlet ports are provided in the fluid channel to receive tubing through which fluid flows into and out of the channel.

When such a fluid warming system is put to use with the fluid warming cassette placed or positioned in the heating region, heat is transferred from the warming unit to and through the cassette to heat fluid as it flows through the fluid channel. In the heating region, heat is transferred by one or more modes including conduction, convection, and radiation. Typically a warming unit is designed for a principal mode of heat transfer to the external surfaces of the cassette. The cassette is constructed for transferring heat to the fluid by conduction from its external surfaces through the layers of the fluid container. One example of a warming unit designed for heat transfer by conduction includes metal plates and means for electrically warming the plates. The metal plates are positioned in an opposing disposition for close frictional contact with one or more surfaces of a cassette. Typically, the plates are slightly separated to define a thin slot into which the cassette may be slid. When the cassette is positioned in contact with the plates while the plates are warmed, heat flows from the plates to the cassette surfaces and through the cassette to the fluid channel, thereby heating fluid as it flows through the channel. To maximize the thermal efficiency and thermal responsiveness of a fluid warming system with a slotted warming unit in which a fluid warming cassette is disposed for conductive heat transfer from the warming unit, the distance between the plates is usually kept very small. This necessitates a fluid warming cassette with a thin, flat fluid container. One such cassette is disclosed in U.S. patent application Ser. No. 09/415,558, entitled "PRESSURE TOLERANT PARENTERAL FLUID AND BLOOD CONTAINER FOR A WARMING CASSETTE", by Augustine et al., filed on Oct. 8, 1999, which is incorporated herein by this reference.

A number of design parameters are important to maximizing the thermal conductivity at the interface between the plates of a conductive warming unit and the fluid warming cassette. For example, very thin films of thermally conductive plastic materials are typically used to reduce the thickness of the container and the length of the thermal conduction path through the container to the fluid channel. A design goal is to maximize the total external surface area of the fluid container which contacts the plates in order to maximize heat transfer to the container, and to invest the structure of the container with the ability to maintain that surface area in contact with the plates in the face of variations in the pressure of fluid flow. This leads to the selection of plastic sheets formed from relatively rigid plastic materials. In this regard, a rigid plastic is as defined in *Whittington's Dictionary of Plastics, Third Edition*, as one with a modulus of elasticity either in flexure or in tension greater than 700 MPa (100 kpsi) at 23° C. and 50% relative humidity when tested in accordance with ASTM methods D747, D790, D638, or D882 (ASTM D833). The same definition gives other specifications for rigid vinyl.

In use, such a fluid container is operated by provision of fluid under positive pressure to its inlet port, which causes the fluid to flow through the container and keeps the fluid channel open. The pressure is positive with respect to ambient pressure, and is usually provided either by a fluid reservoir elevated above the fluid container, or by an infusion pump. When deployed for pediatric cases, in combination with a pressure cuff presently-available cassettes may quickly infuse a large amount of fluid into a small patient, causing undesirable effects and, possibly, harm. One way to limit the volume which may be delivered to an infant or child is to limit the amount of fluid delivered at some maximum pressure by limiting or reducing the cross-sectional dimensions of the fluid flow path of a cassette. This, however can lead to other problems in other circumstances.

It is frequently useful to apply a negative pressure through the outlet side of the fluid warmer cassette in order to draw fluid through the fluid channel. Such negative pressure may be applied, for example, with a syringe coupled to the outlet port through a three-way valve and a piece of tubing. This configuration is used in cases where fluid must be cleared from the cassette, and in cases where a bolus of warmed fluid is to be drawn through the cassette, into the syringe. Negative pressure however interacts adversely with certain structural features of presently-available cassettes. Cassettes made by welding thin films of rigid plastic over rigid spacers exhibit collapse of their fluid channels in response to negative pressure. The collapse is usually profound: it extends along the entire length of the fluid channel.

One way to reduce the tendency of the fluid channel to collapse in response to negative pressure is to increase the thickness and rigidity of the film layers of which the fluid container is constructed. However, the thicker, rigid materials significantly increase heat transfer impedance. During the manufacturing and assembly processes the thicker, rigid materials also result in increased dimensional tolerances, which lead to reduction in contact between these materials and the warming plates caused by material and hardware tolerances. Furthermore, it is difficult to make a fluid channel from plastic films that are altogether resistant to negative pressure, and any bowing or partial collapse of a fluid channel under negative pressure will further reduce surface contact between the film layers and the warming plates.

The application of negative pressure to a warming cassette fluid container made of rigid plastic will cause some degree of contraction along the entire length of the fluid flow path. Unless the rigid fluid container is evenly preloaded against the plates of a warming unit, this contraction will pull the surface of the fluid container away from the plates precisely when warming is required, that is when fluid is being drawn through the fluid path. It is possible to make the fluid container slightly oversized with respect to the slot between the plates, which will preload it against the plates. But this produces difficulty in inserting the cassette between the plates. In some instances, warming units are made with separable plates that can be clamped onto a warming cassette. However, such mechanisms are costly and require a higher incidence of maintenance than mechanisms with fixed plates.

Manifestly, then, there is a need for an effective fluid warming cassette useful in a parenteral fluid warming system in which fluid continues to flow when the cassette is received in a slot between warming unit plates and negative pressure is applied to the outlet port for priming the fluid path or for drawing a bolus. It would be further advantageous if the fluid flowing through the fluid warming cassette in response to this negative pressure would also be warmed. Additional advantage would be gained if the priming volume of the fluid warming cassette were such that the flow path could be primed with a standard syringe.

It would also be advantageous if the fluid warming cassette could be designed for insertion between close-set parallel plates of a warming unit, yet be thin enough to efficiently transfer heat by conduction from the plates to the fluid during negative pressure.

SUMMARY OF THE INVENTION

A fluid warming cassette useful in a system for warming parenteral fluids is provided. The novel fluid warming cassette is particularly useful for warming systems that encounter negative pressures during operation. The novel fluid warming cassette solution for a fluid warmer offers several benefits of the existing design. It allows for fluid to be drawn through the device in response to negative pressure introduced into the fluid channel by way of, for example, a syringe; it allows for warming of the fluid flowing in response to negative pressure; and it provides a reduced priming volume. The fluid warming cassette of this invention is a fluid container in which two sheets of plastic material are joined against a planar spacer to define a fluid channel. The invention is characterized in that at least one of the sheets and the spacer are composed of flexible plastic materials. The flexible spacer defines the flow path and is of sufficient thickness to prevent the outer sheets coming completely together when negative pressure is applied to the fluid channel.

The flexibility of the spacer and sheets also produces a useful response in the cassette to the introduction of negative pressure into the flow path through one of the ports. The flexibility of the sheets in relation to the spacer permit a partial contraction of the flow path that decreases with the distance from the port, without collapse of the entire flow path or occlusion of the flow path.

DETAILED DESCRIPTION OF THE INVENTION

Figure 1:
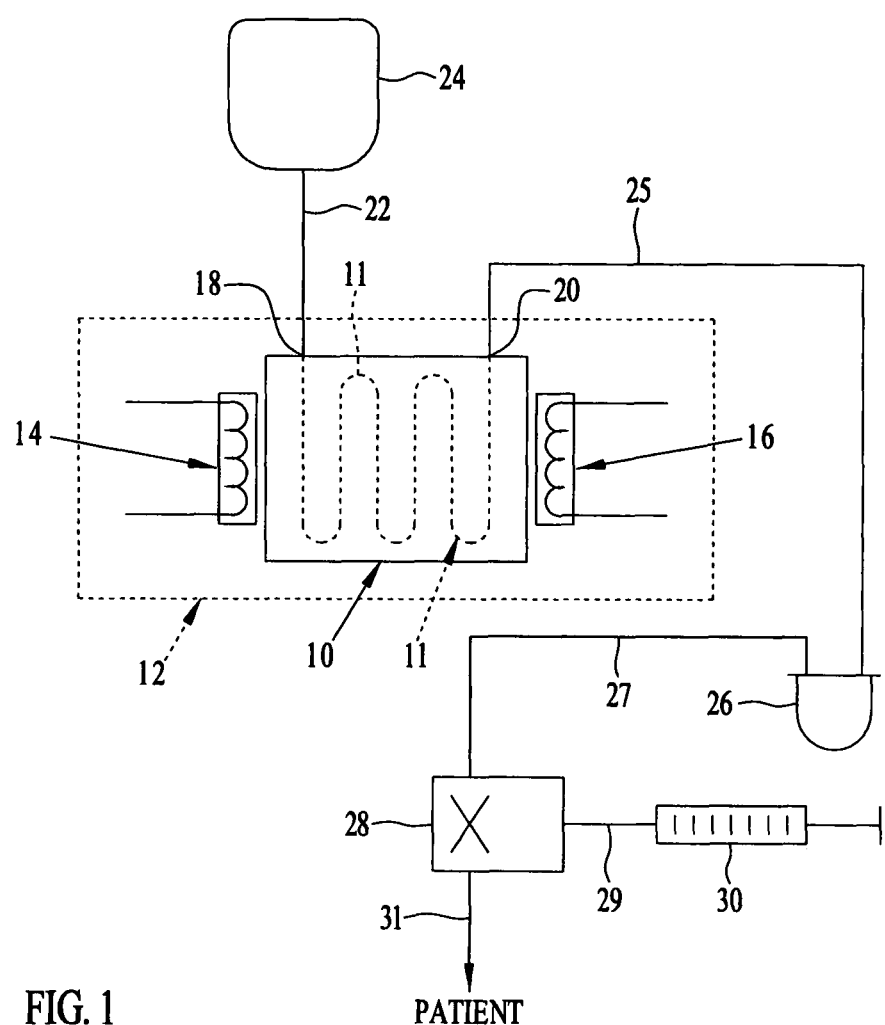
FIG. 1 is partially schematic illustration of a parenteral fluid warming system in which a fluid warming cassette according to the invention is deployed.

This invention is a fluid warming cassette intended for use with a fluid warming unit to warm fluids for intravenous infusion. It is expected that the invention will be particularly useful with pediatric patients. The fluid warming cassette is designed for a small priming volume and is for use with a conductive warming unit, having plates for heating the cassette by conduction disposed in an opposing, spaced-apart configuration, separated by a thin laminar space defining a slot. In use, the fluid warming cassette is received in the slot, in close contact with the plates for transfer of heat by conduction from the plates to the fluid warming cassette.

The fluid warming cassette includes a fluid container having a serpentine fluid flow channel with an inlet port and an outlet port. Fluid flows into the fluid container through the inlet port, and out of the container through the outlet port. The fluid container includes two opposing, thermally conductive sheets of material and a spacer defining an internal serpentine opening. At least one of the sheets is composed of a flexible plastic. Preferably, the spacer is a planar piece; preferably the spacer is also composed of a flexible plastic material, but one that may have a different composition than that of the flexible plastic sheet. The sheets of material are bonded or otherwise joined over or against the spacer, sandwiching it and enclosing the internal serpentine opening to create a fluid channel. A fluid channel with a serpentine pattern is illustrated in the drawings of this application, although other patterns are contemplated.

Refer to FIG. 1 for an understanding of a parenteral fluid warming system that includes a fluid warming cassette according to the invention. In the figure, a source 24 of parenteral fluid under positive pressure is connected by a first line or tube 22 to a fluid warming cassette 10 disposed in a warming unit 12 between plates 14 and 16 that may be warmed by resistive heating means. The plates 14 and 16 define a narrow slot in which the cassette is disposed in close physical contact with the plates. A second line or tube 25 connects the cassette to a bubble trap 26. The bubble trap 26 is connected by a third line or tube 27 to the first port of a three-way valve 28. A second port of the three way valve 28 is connected through a fourth line or tube 29 to a syringe 30. A third port of the valve 28 is connected to a fifth line or tube 31 which may have a needle or joint (neither shown) connected to an end for delivery of fluid to a patient.

With further reference to FIG. 1, the steps used to deliver the fluid from a source to a patient are illustrated schematically. The source 24 is illustrated as an IV bag suspended above the fluid warming cassette 10 for delivery of fluid under positive pressure to an input port 18 of the fluid warming cassette 10. The source 24 may also be embodied as an infusion pump. As fluid flows through the line or tube 22, it enters a fluid flow path 11 in the cassette. The plates 14 and 16 warm the cassette 10 and heat is conducted through the cassette 10 to warm fluid flowing through the fluid flow path 11. Fluid under positive pressure flows in the fluid flow path 11, warming as it approaches the outlet port 20. Warmed fluid flows through the outlet port 20 and into line or tube 25, then through the optional bubble trap 26 where bubbles are removed from the warmed fluid as it flows through the trap 26, into the third line or tube 27. The warmed fluid is conducted through the third line or tube 27 to the first port of the three-way valve 28. The fluid flows from the three-way valve in the fifth line or tube 31 to the patient.

The three-way valve 28 has three selectable modes of operation, each selected by manual or automatic operation of a valve configuration controller (not shown). In a first mode of operation, fluid flows into the first port, through the valve 28 to, and out of the third port into the fifth line or tube 31. In a second mode of operation, determined by a second selectable setting on the valve 28, fluid flows into the first port, through the valve 28 to, and drawn out of the second port into the syringe 30 through the fourth line or tube 29. In a third mode of operation, fluid flows from the syringe 30 into the second port, through the valve 28 to, and out of the third port into the fifth line or tube 31 to the patient. The 3-way is only one solution to accomplishing this. You could use a series of one-way check valves for instance.

Operation of the parenteral fluid warming system of FIG. 1 has three modes, each enabled by a respective setting of the three-way valve 28. The modes are combined as a series of steps to deliver fluid to the patient. In a first mode, determined by the first valve setting, fluid under positive pressure flows from the fluid source 24 through the warming cassette 10, where it is warmed as it flows, through the bubble trap 26, into the first port of the valve 28 through the third line or tube 27 and out of the third port of the valve 28 through the fifth line or tube 31 for infusion into a patient. In a second mode of operation, determined by the second valve setting, a negative pressure is applied to the fluid flow path by drawing the plunger of the syringe outwardly from the syringe 30. This draws fluid from the fluid source 24 through the warming cassette 10 under negative pressure, where it is warmed as it flows, into the first port of the valve 28 through the third line or tube 27, and out of the second port into the syringe 30 through the fourth line or tube 29. In the third mode of operation, determined by the third valve setting, warmed fluid is forced from the syringe 30 through the fourth line or tube 29 through the valve 28 and out of the third port of the valve 28 through the fifth line or tube 31 for infusion into a patient.

The three-way valve 28 may be bypassed altogether and the syringe 30 may be attached directly to the output port 20 of the cassette 10, through a tube or manifold (neither shown) to withdraw fluid from the fluid warming cassette 10, which will also introduce a negative pressure into the flow path 11.

In operation, a negative pressure is applied to the fluid flow path by drawing the plunger of the syringe outwardly from the syringe 30. This draws fluid from the fluid source 24 through the warming cassette 10 under negative pressure, where it is warmed as it flows and drawn into the syringe 30. The syringe 30 provides the ability for a clinician to practice "syringe dosing" which allows exact measurement of a quantity of warmed fluid (also called a "bolus") to be drawn into the syringe and administered therefrom. Syringe dosing is important in pediatrics where patient blood volume is very small and the infusion of excessive fluids or fluids in the wrong ratio could harm the patient. The syringe 30 may also be used for priming the fluid warming cassette 10. Another form would be that the fluid is drawn from the three-way valve 28 or output port 20, the syringe is then removed from the valve or port and administered through yet another port.

In the cases where negative pressure is applied to the fluid warming cassette, profound failure of fluid flow in the fluid flow path in prior art fluid containers can result. In these cases, the rigid plastic of which the containers are made causes the fluid flow path to resist the negative pressure, which is thereby distributed along the entire flow path. The flow path resists until a certain maximum distribution of negative pressure is reached, at which point the entire flow path may collapse, completely shutting off the flow of fluid. In the cases where the plastic is rigid and/or thick enough to resist collapse, deformation of the flow path may occur along its entire length, causing separation between the fluid container and heating plates, which leads to a substantial increase in the thermal resistance between the plates and the fluid container and failure to heat the fluid sufficiently.

The unique design of the fluid warming cassette of this invention permits partial collapse of the fluid flow path without complete occlusion, thereby supporting fluid flow even with the introduction of negative pressure. The amount of collapse or resistance can be tuned by changing the geometry of the channels. For example, the wider the channel, the more the collapse should be apparent.

Figure 2:
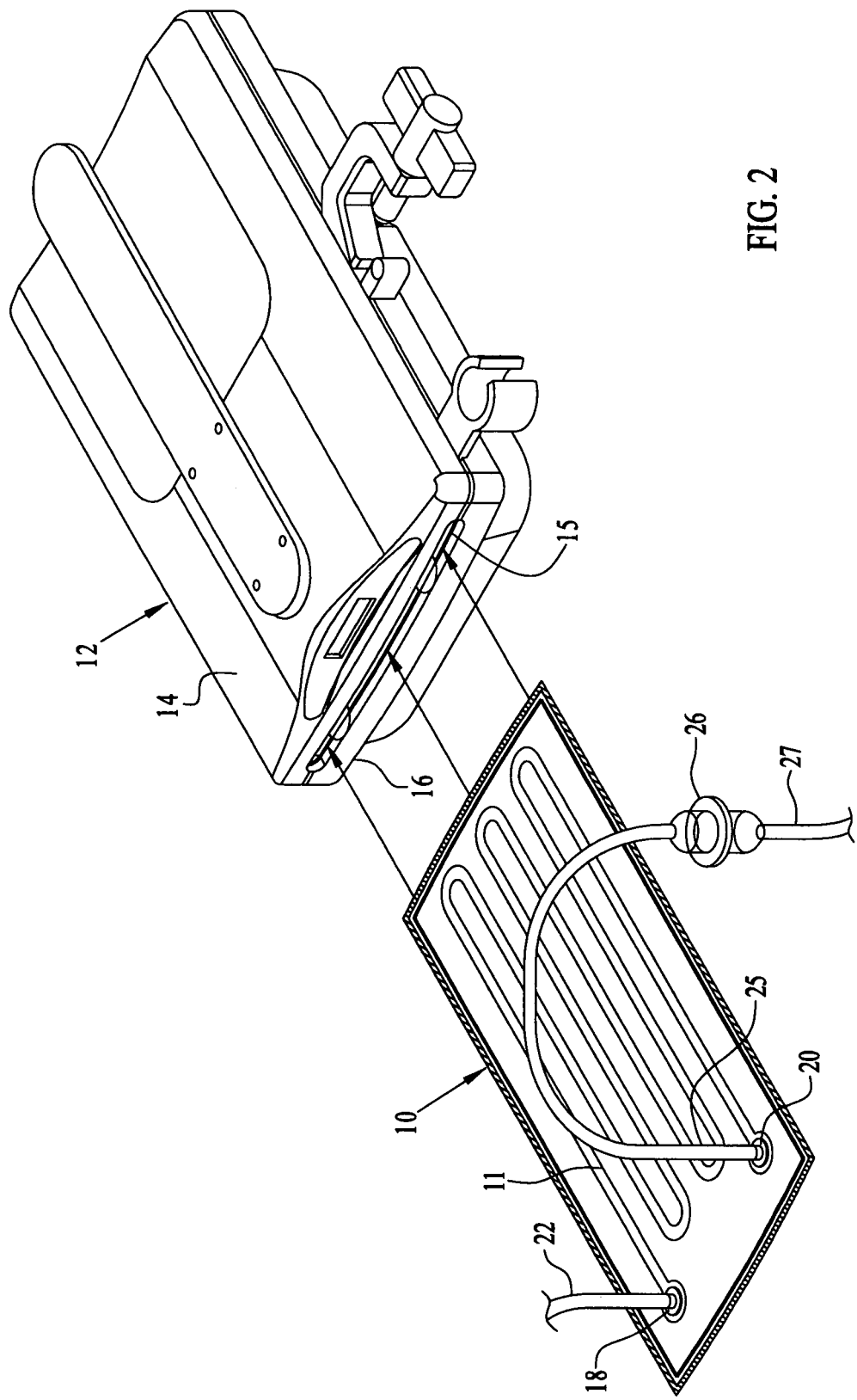
FIG. 2 is a perspective view of a fluid warming cassette according to this invention disposed for use with a fluid warming unit.

FIG. 2 is a perspective illustration of a fluid warming cassette 10 with a fluid channel 11 according to the invention for use with a fluid warming unit 12 having warming plates 14 and 16. The plates 14 and 16 are spaced apart at a fixed distance 15, and the fluid warming cassette 10 is inserted between the plates 14 and 16 so that fluid flowing in the fluid warming cassette 10 is heated by conduction from the plates 14 and 16.

The fluid warming cassette 10 includes an inlet port 18 and an outlet port 20 that are in fluid communication with the fluid channel 11. A fluid inlet tube 22 may be attached to the inlet port 18. The other end of the fluid inlet tube 22 may be attached to a fluid source 24 of pressurized fluid (see FIG. 1). A fluid outlet tube 25 may be attached to the outlet port 20.

Figure 3:
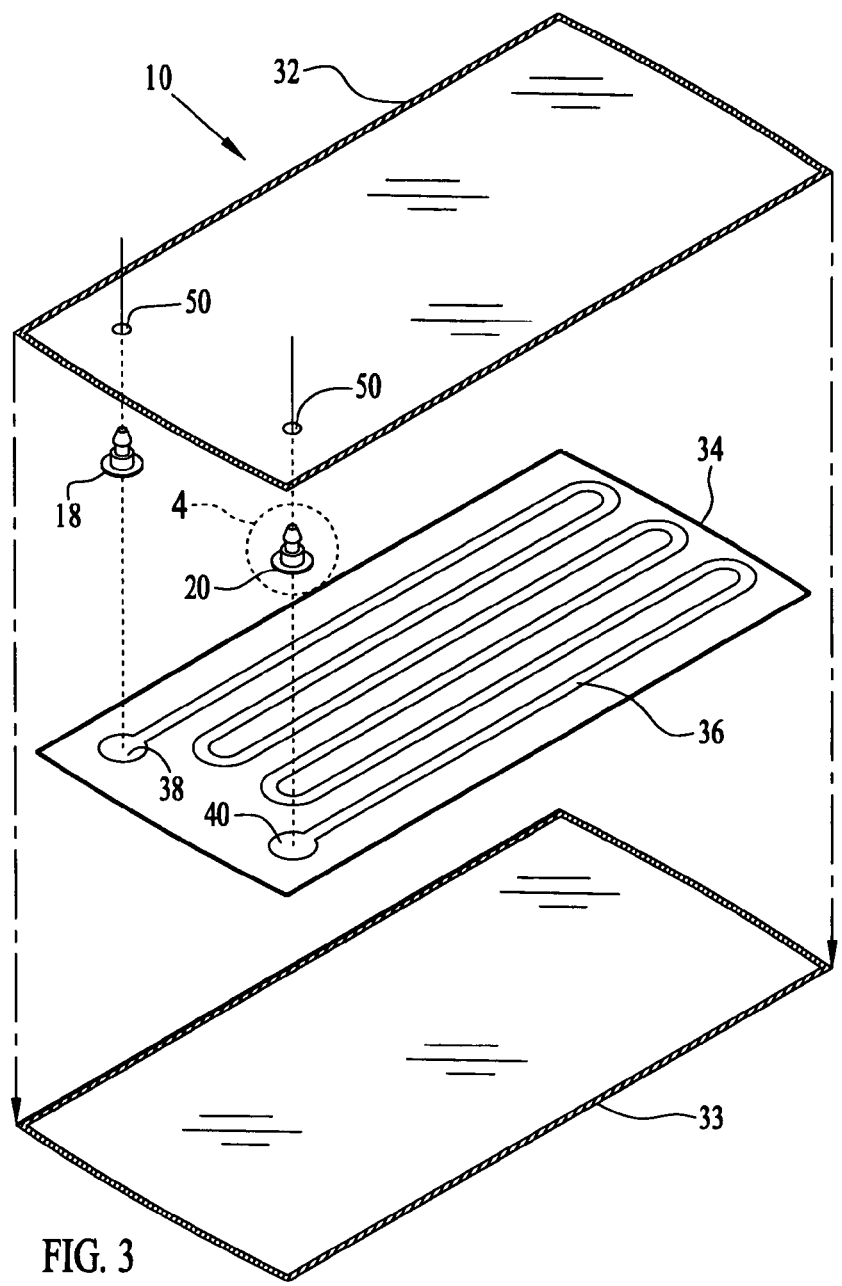
FIG. 3 is an exploded view of the fluid warming cassette of FIG. 2.
Figure 4:
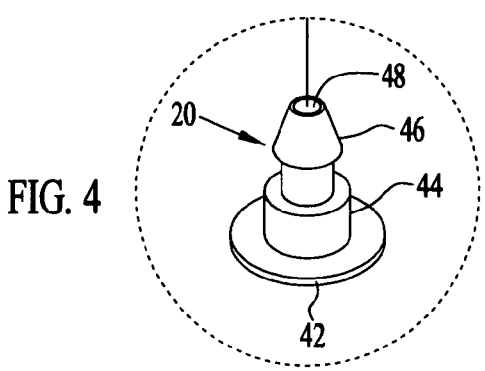
FIG. 4 is a more detailed depiction of the fluid inlet port of FIG. 3.

FIG. 3 is an exploded view of the fluid warming cassette 10 of FIG. 2 showing its elements. The cassette 10 includes a first sheet 32, a second sheet 33, a planar spacer 34, the inlet port 18 and the outlet port 20. The spacer 34, preferably a planar piece, includes an internal serpentine opening 36 having an inlet area 38 and an outlet area 40. FIG. 4 shows an enlarged view of outlet port 20, which includes a disk shaped base 42, an upstanding portion 44 extending from the base 42 with a barbed end 46, and a fluid hole 48 extending through the outlet port. The inlet port 18 is substantially similar to the outlet port 20. The first sheet 32 includes holes 50 proximate the inlet 38 and outlet areas 40, the holes 50 being dimensioned to accept the upstanding portion 44 of the inlet or outlet ports. The ports may also be welded in place.

Figure 5:
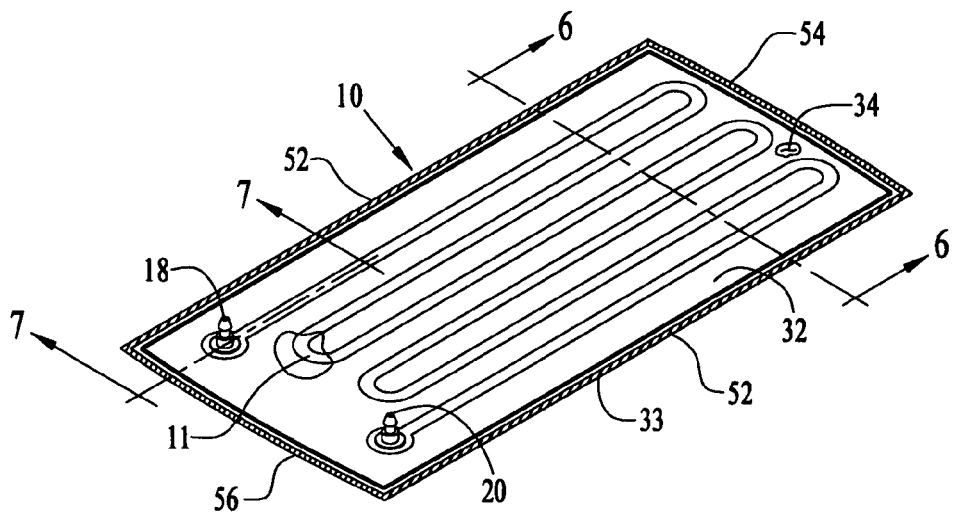
FIG. 5 is a perspective view of the fluid warming cassette of FIG. 2.

FIG. 5 shows the assembled fluid warming cassette. To assemble the fluid warming cassette 10, the spacer 34 is disposed between the first 32 and second 33 sheets, with the inlet 18 and outlet 20 ports positioned in the inlet and outlet areas 38 and 40, and the upstanding portions 44 extending through the holes 50. In one embodiment, a heat sealing platen, impulse heat sealer, RF platen, or US horn is applied, joining the sheets around their peripheries to form a periphery of the cassette including sides 52, distal end 54 and proximal end 56. Once joined, the first sheet 32 and the second sheet 33 enclose the spacer 34 forming the fluid channel 11. Optionally, the sheets may be joined around their peripheries with an adhesive boundary forming a second barrier.

In another embodiment, the first sheet 32 and the second sheet 33 are joined to the spacer 34 with an adhesive. The first sheet 32 and second sheet 33 enclose the internal serpentine opening 36, forming the fluid channel 11. When this sealing is done in conjunction with the sealing of the periphery of the sheets, as disclosed above, a double barrier is formed, the periphery seal forming a second barrier. Optionally, with the compatible material choices, the first sheet 32 and second sheet 33 may be thermally bonded to the spacer 34.

Figure 6:
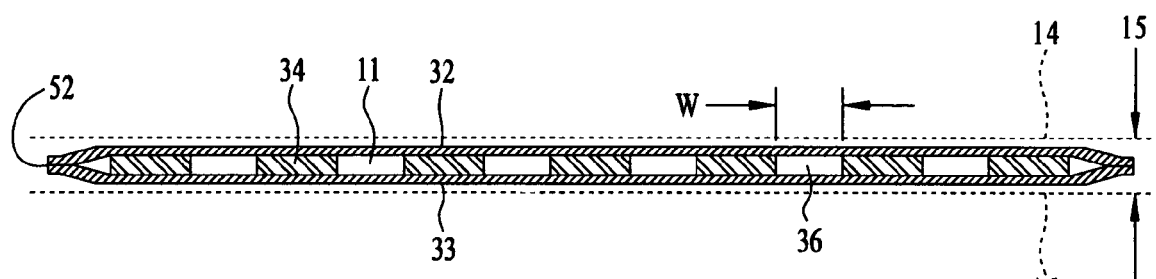
FIG. 6 is a cross-section of FIG. 5 showing the fluid channel.

FIG. 6 is a cross-sectional view of FIG. 5 showing the assembled fluid warming cassette 10. The first sheet 32 and the second sheet 33 are joined along the periphery 52 by thermal bond, adhesive, or other suitable methods. The spacer 34 with the internal serpentine opening 36 is positioned between the first sheet 32 and the second sheet 33, forming the fluid channel 11. Optionally, the first sheet 32 and the second sheet 33 may be attached to the spacer 34 by thermal bond, adhesive, or other suitable means. As shown in the figure, the dimensions of the internal serpentine opening 36 is such that the first sheet 32 and the second sheet 33 will not completely collapse or touch each other across the fluid path when there is negative pressure in the fluid warming cassette 10. Also shown in FIG. 6 is the relative position of the warming plates 14 and 16, shown in phantom.

Figure 7:
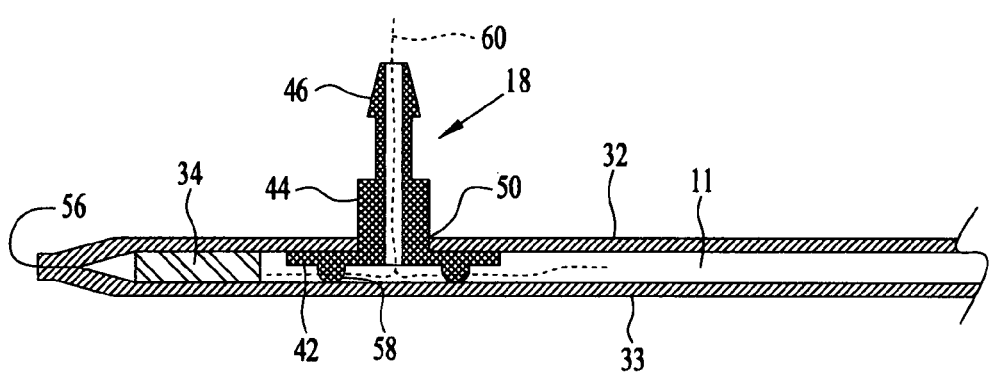
FIG. 7 is a cross-section of FIG. 5 showing details of the inlet port.

FIG. 7 is a cross-sectional view showing the inlet port 18 installed in the fluid warming cassette 10. This same description applies to the outlet port 20. As described previously, the first sheet 32 includes holes 50 dimensioned such that the upstanding portion 44 of the inlet 18 and outlet 20 ports extend through the first sheet 32, the disk shaped base 42 preventing the ports from coming out. The fluid inlet tube 22 or the fluid outlet tube 25 may be attached to the barbed end 46. The disk shaped base 42 also includes a plurality of bumps 58 on the surface opposite the upstanding portion 44. Alternatively, grooves may be used instead of the bumps. The grooves or bumps 58 prevent the second sheet 33 from completely covering the fluid hole 48 during use. Dotted line 60 shows the fluid flow path into or out of the fluid warming cassette 10. During negative pressure, the fluid is extracted from the fluid warming cassette 10 from the outlet port 20. This negative pressure tries to collapse the internal fluid channel 11 by drawing the first 32 and second 33 sheets toward each other. In addition, the second sheet 33 is pulled toward the disk shaped base 42. The plurality of bumps 58 prevent the second sheet 33 from covering the fluid hole 48.

The first sheet 32 and second sheet 33 may be made from one or more materials selected from the group consisting of polyester, polyamide (Nylon®, DuPont), polyethylene glycol terephthalate (PETG)(Mylar®, DuPont), metal foils, ionomer resins (Surlyn®, DuPont), modified polyolefin (for example mPE), polyethylene (PE), polypropylene (PP), polyvinyl chloride (PVC), polyurethane, polycarbonate (PC), modified acrylic, and ethyl vinyl acetate (EVA) co-polymer. Preferably each of the thermally conductive sheets is relatively thin, for example 0.004 in. (4 mil) thick, or less.

The preferred embodiment of the spacer 34 is a planar piece made from a high-density polyethylene (HDPE), or other material that would define the flow path and maintain space between the sheets. The spacer 34 may be molded, or if desired, die cut, to form the shape and the internal serpentine opening 36. In one embodiment, the internal serpentine opening 36 has a centerline length of approximately 56 inches and a width W of approximately 0.3 inches. The fluid channel 11 is formed when the internal serpentine opening is covered by the first sheet 32 and second sheet 33. The priming volume of the fluid channel is much smaller than the other fluid warmers, less than 15 cc's, preferably 11-13 cc's. This small priming volume allows clinicians to purge the fluid warmer with a standard 20 cc syringe. In a typical configuration, the total priming volume of a disposable set (including the fluid channel 11, the fluid inlet tube 22 and the fluid outlet tube 25) is approximately 20 cc. This may also allow clinicians to purge the disposable set with a standard 20 cc syringe.

In use, the fluid warming cassette 10 is inserted into the warming unit 12 by orienting and sliding the distal end 54 of the warming cassette 10 inwardly between the plates 14 and 16, with the inlet port 18 and outlet port 20 being position outside of the warming unit 12. To aid in the insertion and removal of the fluid warming cassette 10 in the fluid warming unit 12, it may be advantageous to have a handle and/or stiffening members, such as those described in U.S. Pat. No. 6,464,666, which is incorporated herein by reference. In addition, the fluid warming cassette 10 may include the bubble trap 26 attached to the handle, also disclosed in U.S. Pat. No. 6,464,666, which traps any air bubbles that may have inadvertently been introduced into the inlet tubing from the IV bag or may have been created by "out-gassing" during the warming of the fluids.

Other variations and embodiments of the present invention will occur to those skilled in the art with reflection upon the disclosed examples of the present invention cassette fluid container and formation of such a cassette fluid container.

We claim:

1. A fluid warming cassette with proximal and distal ends, the fluid warming cassette consisting of:
  a flexible planar spacer having an internal serpentine opening;
  a first sheet formed of flexible plastic material proximate the planar spacer;
  a second sheet of flexible plastic material joined to the first sheet to enclose the planar spacer and form a serpentine fluid channel with a serpentine fluid channel having first and second ends near the proximal end;
  an inlet port in fluid communication with the first end; and
  an outlet port in fluid communication with the second end.

2. The fluid warming cassette of claim 1, wherein the first and second sheets are joined along their peripheries.

3. The fluid warming cassette of claim 2, wherein the first and second sheets are also joined to the spacer.

4. The fluid warming cassette of claim 1, wherein the first and second sheets are made from a material selected from the group consisting of polyester, polyamide (Nylon®, DuPont), polyethylene glycol terephthalate (PETG) (Mylar®, DuPont), metal foils, ionomer resins (Surlyn®, DuPont), modified polyolefin (for example mPE), polyethylene (PE), polypropylene (PP), polyvinyl chloride (PVC), polyurethane, polycarbonate (PC), modified acrylic, and ethyl vinyl acetate (EVA) co-polymer.

5. The fluid warming cassette of claim 1, wherein the spacer is made from a closed cell foam.

6. The fluid warming cassette of claim 1, wherein the spacer is made from a high-density polyethylene.

7. The fluid warming cassette of claim 1, wherein the serpentine opening is dimensioned such that the first and second sheets do not completely touch each other within the serpentine fluid channel when there is a negative pressure in the fluid channel.

8. The fluid warming cassette of claim 7, wherein the width of the internal serpentine opening is less than 0.3 inches.

9. The fluid warming cassette of claim 1, wherein the fluid channel has a priming volume less than 15 cc.

10. The fluid warming cassette of claim 1, wherein the internal serpentine opening includes an inlet area at the first end and an outlet area at the second end, the inlet port being positioned in the inlet area and the outlet port being positioned in the outlet area.

11. The fluid warming cassette of claim 10, wherein each of the inlet and outlet ports includes:
   a base having a shape with a first side facing the first sheet and a second side facing the second sheet;
   an upstanding portion extending from the first side, through the first sheet;
   a fluid hole through the upstanding portion and the base; and
   means for preventing the second sheet from covering the fluid hole.

12. A fluid warming cassette, comprising:
   proximal and distal ends;
   a flexible planar spacer having an internal serpentine opening;
   a first sheet formed of flexible plastic material proximate the planar spacer;
   a second sheet of flexible plastic material joined to the first sheet to enclose the planar spacer and form a serpentine fluid channel with a serpentine fluid channel having inlet and outlet areas near the proximal end;
   an inlet port in the inlet area for being attached to an inlet tube; and
   an outlet port in the outlet area for being attached to an outlet tube.

13. The fluid warming cassette of claim 12, wherein the first and second sheets are joined along their peripheries.

14. The fluid warming cassette of claim 13, wherein the first and second sheets are also joined to the spacer.

* * * * *